United States Patent
Shishido et al.

(10) Patent No.: US 7,483,560 B2
(45) Date of Patent: Jan. 27, 2009

(54) METHOD FOR MEASURING THREE DIMENSIONAL SHAPE OF A FINE PATTERN

(75) Inventors: Chie Shishido, Yokohama (JP); Ryo Nakagaki, Kawasaki (JP); Maki Tanaka, Yokohama (JP); Kenji Watanabe, Oume (JP); Yuya Toyoshima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 685 days.

(21) Appl. No.: 10/679,290

(22) Filed: Oct. 7, 2003

(65) Prior Publication Data
US 2005/0100205 A1   May 12, 2005

(30) Foreign Application Priority Data
Jan. 17, 2003   (JP) .................. 2003-008998

(51) Int. Cl.
*G06K 9/00* (2006.01)
(52) U.S. Cl. .................................... 382/145
(58) Field of Classification Search ............... None
See application file for complete search history.

(56) References Cited

U.S. PATENT DOCUMENTS

| | | | | |
|---|---|---|---|---|
| 5,675,377 A | * | 10/1997 | Gibas ........................ | 348/47 |
| 6,651,226 B2 | * | 11/2003 | Houge et al. ................ | 716/4 |
| 6,930,308 B1 | * | 8/2005 | Lorusso et al. .............. | 250/310 |
| 2003/0108235 A1 | * | 6/2003 | Hayes ....................... | 382/145 |

FOREIGN PATENT DOCUMENTS

| | | |
|---|---|---|
| JP | 03-141544 A | 6/1991 |
| JP | 04-342942 A | 11/1992 |
| JP | 2002-506217 A | 2/2002 |

* cited by examiner

*Primary Examiner*—Matthew C. Bella
*Assistant Examiner*—Alex Liew
(74) *Attorney, Agent, or Firm*—Antonelli, Terry, Stout & Kraus, LLP.

(57) ABSTRACT

In a method of measuring a three dimensional shape of an arbitrary fine pattern on a semiconductor device, an optical measurement system carries out a measurement to obtain cross-section information, and an electron microscope obtains an electron beam image of the arbitrary fine pattern. Plane information and cross-section information obtained from the electron beam image of the arbitrary fine pattern are combined to measure the three dimensional shape of the arbitrary fine pattern.

14 Claims, 13 Drawing Sheets

FIG.4
(a) cross sectional shape
(b) signal waveform
(c) first-order differentiation waveform
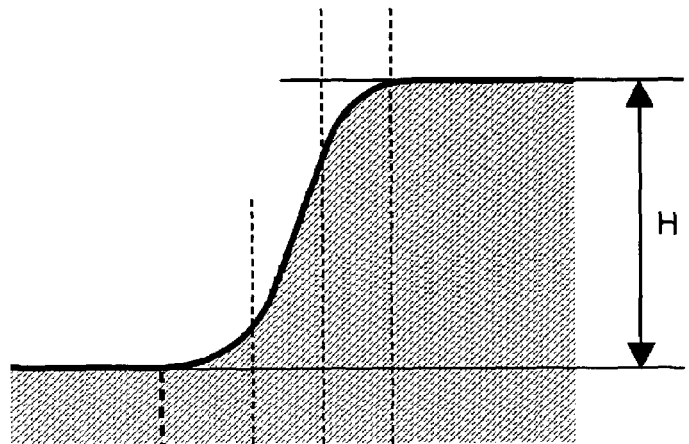
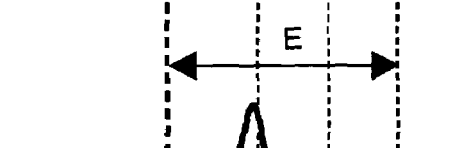
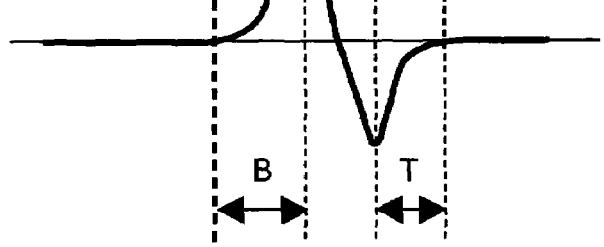
average slope angle: $\tan^{-1}(H/E)$
bottom roundness: $B/H$
top roundness: $T/H$

FIG.5
(a) cross sectional shape
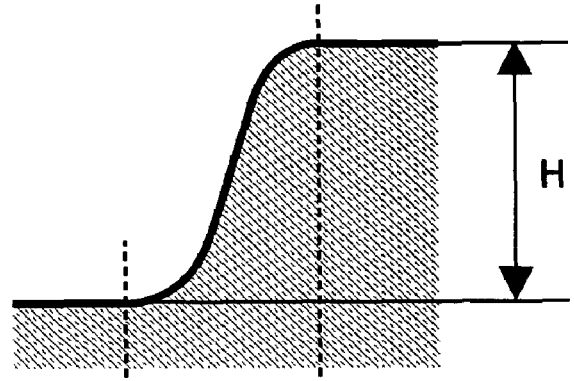
(b) waveform
(c)
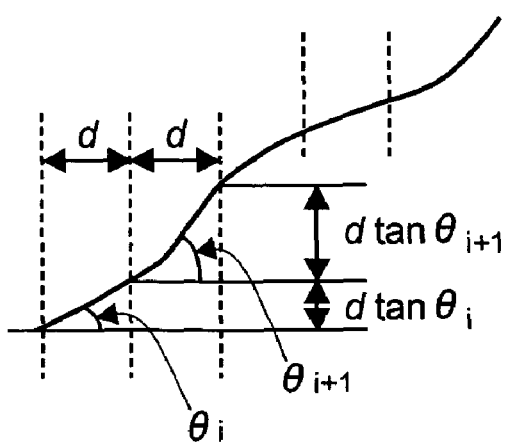
$$SE_i = a \cdot \frac{1}{\cos \theta_i} + b \quad \cdots (5.1)$$
$$H = \sum_{i=0}^{N} d \cdot \tan \theta_i \quad \cdots (5.2)$$

FIG.7
(a) 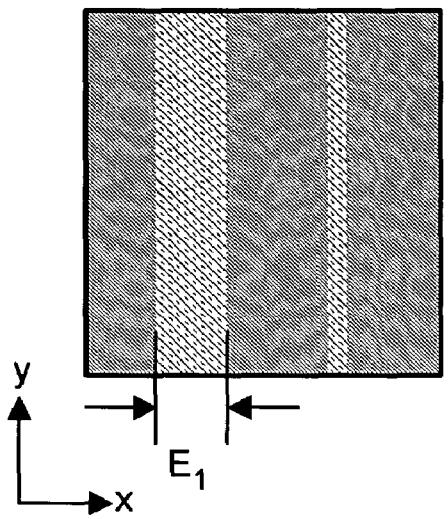
(b) 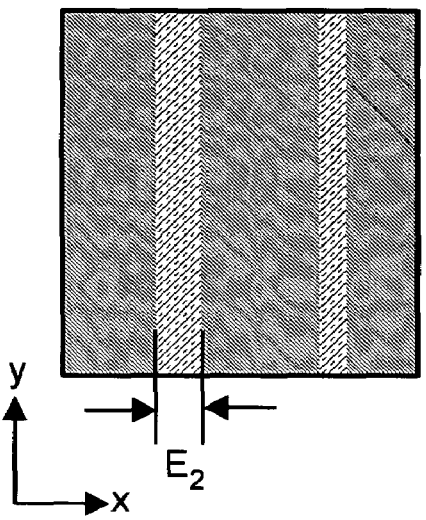
(c) 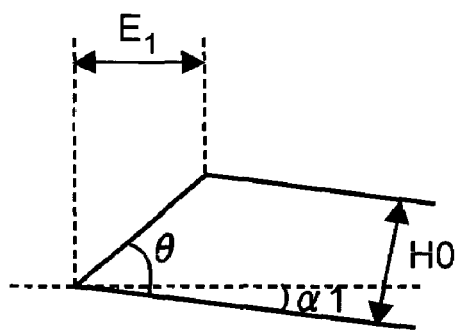
(d) 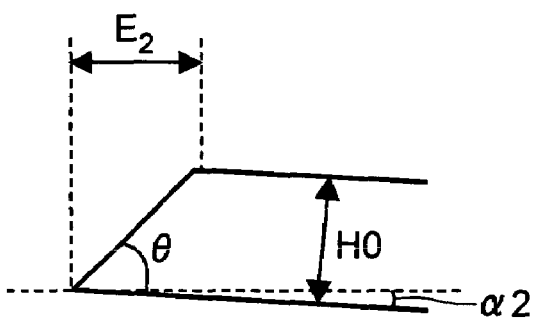
$$\theta = \tan^{-1} \frac{E_1 \cos\alpha_2 - E_2 \cos\alpha_1}{E_1 \sin\alpha_2 - E_2 \sin\alpha_1} \quad \cdots (7.1)$$
$$H_0 = \frac{E_1 \sin\theta}{\cos(\theta + \alpha_1)} \quad \cdots (7.2)$$

FIG.9
(a) 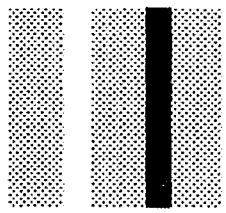
(b) 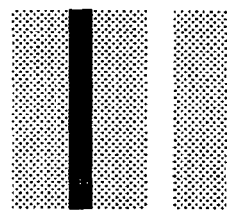
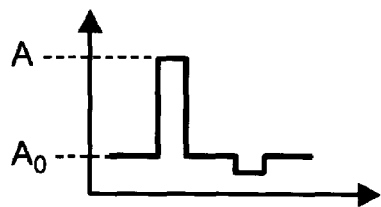
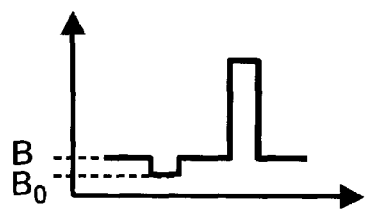
(c)
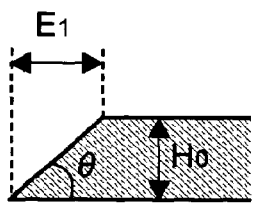
$$\theta = \tan^{-1} K \frac{A^2 - B^2}{A_0 - B_0} \quad \cdots (9.1)$$
$$H_0 = E_1 \tan\theta \quad \cdots (9.2)$$
(d) 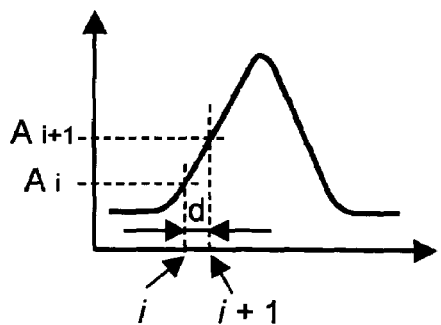
(e) 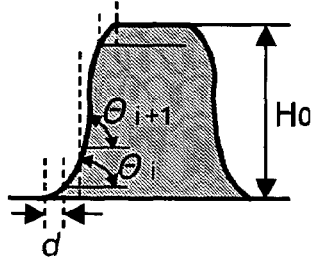
$$\theta_i = \tan^{-1} K \frac{A^2 - B^2}{A_0 - B_0} \quad \cdots (9.3)$$
$$H_0 = d \Sigma \tan\theta_i \quad \cdots (9.4)$$

METHOD FOR MEASURING THREE DIMENSIONAL SHAPE OF A FINE PATTERN

BACKGROUND OF THE INVENTION

The present invention relates to a method which is used for measuring a three dimensional shape of a fine pattern formed on a semiconductor device, such as a semiconductor memory or an integrated circuit.

SEMs (scanning electron microscope) are used for measuring fine patterns that are formed on semiconductor devices. The SEM obtains an electron beam image of a sample by detecting secondary electrons and reflected electrons that are generated when an electron beam is irradiated onto the sample. The most popular SEM used currently in semiconductor processing is called a critical dimension SEM, which measures a sample mainly by using a secondary electron beam image.

FIG. 2 shows the relationship between a cross sectional shape and a secondary electron beam image of a sample. The greater the slope of a surface of the sample, the greater will be the strength of secondary electrons emitted therefrom, so that, as shown in FIG. 2, an image is obtained having bright portions (hereinafter called bright bands) corresponding to side portions (slope portions) of the sample pattern and dark portions corresponding to plane portions of the sample pattern. With the bright bands, the dimensions d1 and d2 are measured to obtain a bottom size and top size of the sample, respectively. However, three dimensional information, such as the height H of the sample and the slope angle θ of the side surface cannot be obtained.

In semiconductor processing, the critical dimension SEM has been conventionally used for optimizing the conditions of a manufacturing machine, such as an aligner and etcher, or for monitoring process fluctuation. However, with refining of the patterns, three dimensional shapes of the samples need to be measured in various cases, wherein the critical dimension SEM is not always useful.

Examples of related technology for measuring cross sectional shapes are as follows.

(1) After a wafer is cut or FIB-processed, a cut surface of the wafer is observed using an electron microscope.

(2) The cross sectional shapes are observed using an AFM (Atom Force Microscope).

(3) The cross sectional shapes are observed using scatterometry. However, in these methods, the following problems are encountered.

In the method (1), it takes a long time to prepare for observation of the cross sections. Additionally, the cut or FIB-processed wafers tend to become contaminated, and, thus, they cannot be completed as products. As a result, this method cannot be used for process fluctuation monitoring in a quantity production process.

The method (2) does not take a longer time than that in the method (1) to observe the cross sections; however, the AFM has a low throughput, which is about ⅓ of that of the popular critical dimension SEM, and it cannot be used to measure all patterns because of restriction of the chip shapes. Consequently, as it is near-meaningless, critical points cannot be measured in the monitoring of process fluctuation in which measurement of three dimensional shapes is required.

Recently, the scatterometry method (3) has received attention, because it can be operated at high speed, and it can be used to measure cross sectional shapes non-destructively. Using the fact that spectral distribution of scattered light from a sample changes depending on the material and cross sectional shape of the sample, the scatterometry method matches the spectral distribution of the actually-measured sample to the spectral distribution library of various cross sectional shaped models previously produced using offline simulations, thereby to indirectly measure the cross-sectional shape of the sample (see FIG. 3). In principle, any pattern shape can be produced. However, current computers cannot generate a library including variations of all patterns. In the present condition, only lines and space patterns uniformly repeated in one direction are measurable. As a result, the scatterometry method is used only for measuring test-specific patterns that are formed on a wafer, and it cannot be used to measure arbitrary patterns (for example, critical points for process fluctuation).

Technology related to the present invention is disclosed in JP-A No. 141544/1991, JP-A No. 342942/1992, and JP-A No. 506217/2002. However, the technology disclosed in these publications have the following problems. The critical dimension SEM, which is popular in semiconductor processing, can measure plane shapes by use of electron beam images of arbitrary patterns, but it cannot be used to measure three dimensional shapes. The scatterometry method can measure three dimensional shapes, but the sample patterns are limited to lines and spaces. Therefore, the scatterometry method can be used to measure only those shapes which conform to the test patterns produced for measurement.

SUMMARY OF THE INVENTION

The present invention provides a method which is capable of measuring a three dimensional shape of an arbitrary fine pattern formed on a semiconductor device, in other words, a method that is capable of measuring a three dimensional shape not limited to a test pattern.

In accordance with the present invention, an optical measurement system, such as a system which uses the scatterometry method, measures cross sectional shape information about a test pattern, an electron microscope obtains an electron beam image of a fine pattern, and plane surface information about the fine pattern is obtained from the electron beam image and is combined with the cross-sectional shape information about the test pattern so as to measure the three-dimensional shape of the fine pattern.

Additionally, in accordance with the present invention, an optical measurement system, such as a system which uses the scatterometry method, measures cross-sectional shape information about a test pattern, an electron microscope obtains an electron beam image of an arbitrary pattern, and the cross-sectional shape information about the test pattern is applied to slope change information about a surface of the fine pattern reflected on the electron beam image, so as to measure the three-dimensional shape of the fine pattern.

Further, in accordance with the present invention, an optical measurement system, such as scatterometry method, measures cross-sectional shape information about a test pattern, an electron microscope also obtains an electron beam image of a test pattern, a relational equation is derived from the cross-sectional shape information and the electron beam image, and the relational equation is applied to an electron beam image of a fine pattern, so as to measure the three-dimensional shape of the fine pattern. Further; in accordance with the present invention, cross sectional shape information about a test pattern is obtained by an optical measurement system, such as a system which uses the scatterometry method, and the obtained information is used as a constraint for calculating a three dimensional shape of a fine pattern through the following methods (1) and (2).

(1) With a plurality of the images that are obtained when a fine pattern tilts at different angles, which images are obtained by an electron microscope having a beam tilt or stage tilt system, a three dimensional shape of the fine pattern is measured based on the principle of triangulation.

(2) With a plurality of reflected electron beam images that are obtained by a plurality of reflected electron detectors, a three dimensional shape of a fine pattern is measured on the principle of photometric stereo processing.

These and other objects, features and advantages of the invention will be apparent from the following more particular description of preferred embodiments of the invention, as illustrated in the accompanying drawings.

BRIEF DESCRIPTION OF THE DRAWINGS

FIG. 4(a) is a diagram which shows a cross-sectional shape of a pattern.

FIG. 4(b) is a signal waveform diagram of a SEM image signal obtained from the pattern of FIG. 4(a).

FIG. 4(c) is a diagram which shows a first-order differentiation waveform obtained by calculating a first-order differentiation of the signal waveform of FIG. 4(b).

FIG. 5(a) is a diagram which shows a cross-sectional shape of a pattern.

FIG. 5(b) is a signal waveform diagram of a SEM image signal of the pattern of FIG. 5(a).

FIG. 5(c) is a diagram which shows a method to be used for calculating a three dimensional shape of a sample from the secondary electron signal strength of a sample.

FIGS. 7(a) to 7(d) illustrate the principle of stereoscopic processing in accordance with the second embodiment of the present invention, in which FIGS. 7(a) and 7(b) are diagrams of electron beam images of a sample, and FIGS. 7(c) and 7(d) are diagrams relating to the images of FIGS. 7(a) and 7(b).

FIGS. 9(a) to 9(e) are diagram which illustrate the principle of the third embodiment of the present invention.

DESCRIPTION OF THE PREFERRED EMBODIMENTS

The present invention will be explained below with reference to the appended drawings.

First Embodiment

Figure 1:
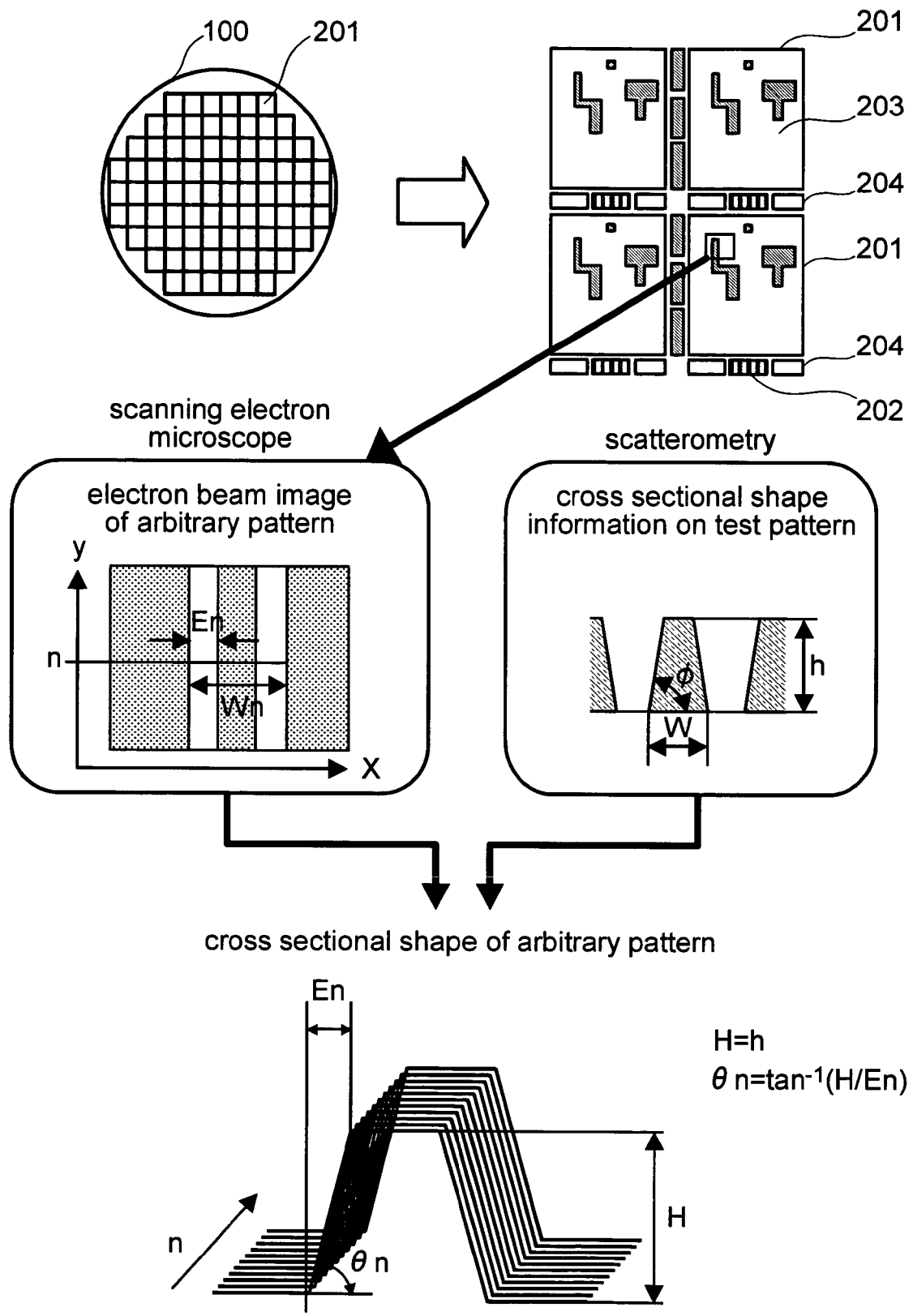
FIG. 1 is a diagram which shows a procedure for measurement in accordance with a first embodiment of the present invention.
Figure 2:
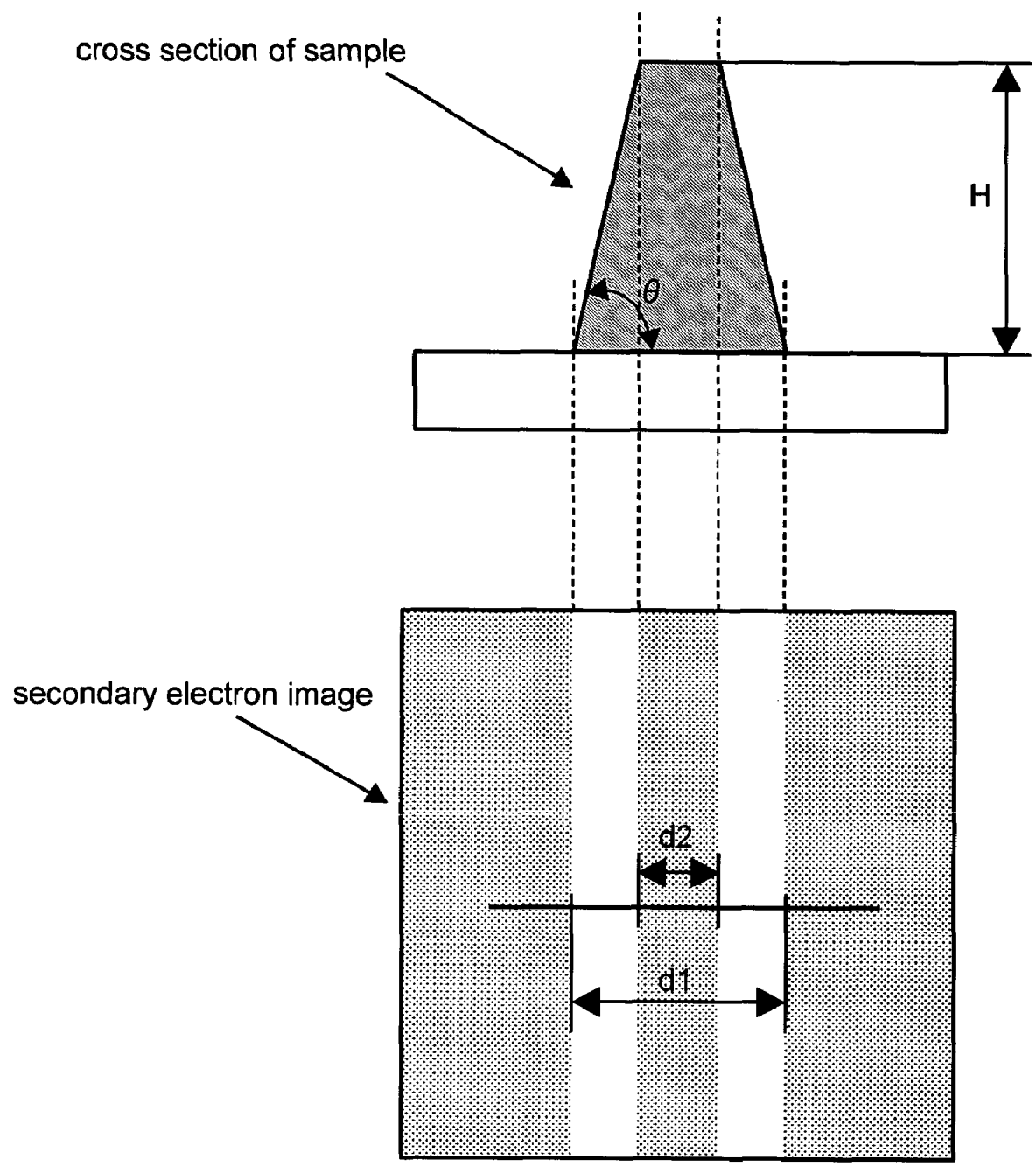
FIG. 2 is a diagram which shows a cross-sectional shape of a measurement sample and a secondary electron beam image thereof, where measurement by a conventional critical dimension SEM is employed.
Figure 3:
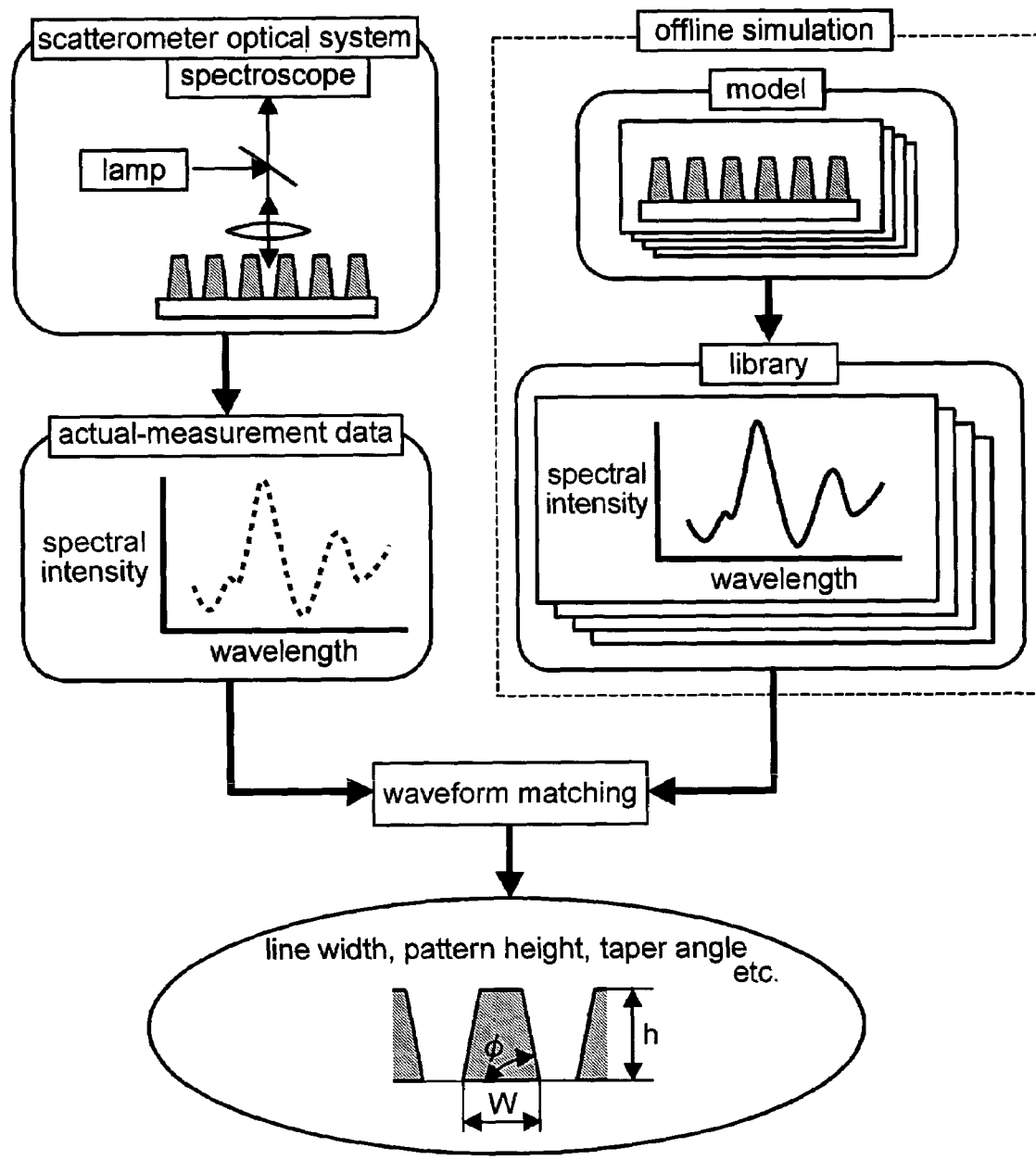
FIG. 3 is a schematic diagram showing the principles involved in the scatterometry method of measurement.

FIG. 1 shows the principles employed in a first embodiment of the present invention. In the manufacture, a large number of semiconductor chips 201 are formed on a wafer 100. A scribe area 204 is formed between the semiconductor chips 201. The scribe area 204 is cut to complete manufacture of the semiconductor chips. A test pattern 202 is formed on the scribe area 204. The test pattern 202 is formed in the same manufacturing process as that used to form a device pattern 203 in the semiconductor chips 201. In other words, the materials of the test pattern 202 and device pattern 203 are the same, and their film thicknesses are almost the same.

As shown in FIG. 1, an electron beam image of a required portion of the scribe area 204 is obtained by a SEM, and the test pattern 202 is measured by scatterometry.

Figure 11:
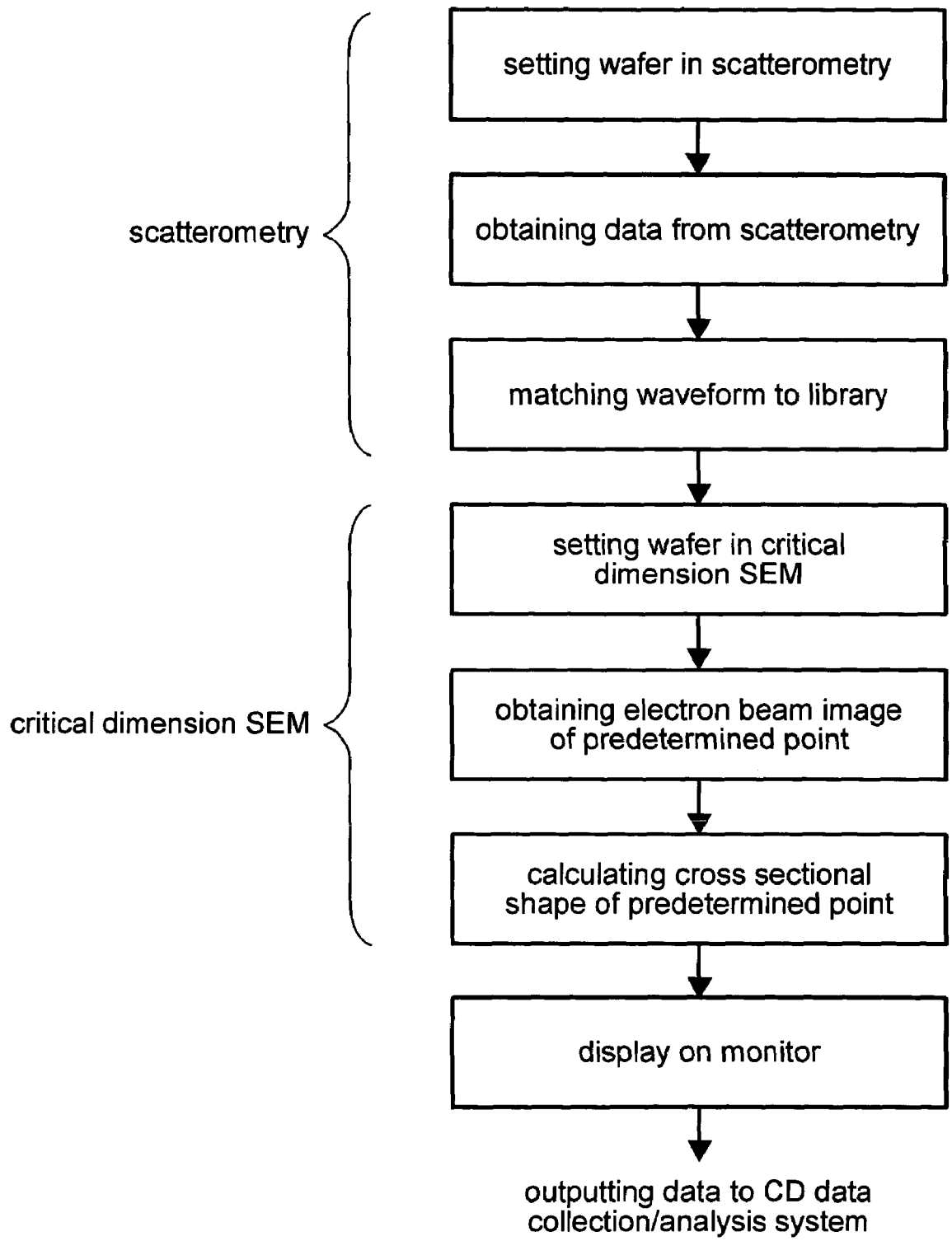
FIG. 11 is a flowchart of a procedure used for measuring a three dimensional shape according to the present invention.

FIG. 11 is a flowchart showing an example of the procedure used for this measurement. The line width Wn and bright band width En of an electron beam image are measured, where n represents a measurement position in the y direction on the image. As shown in FIG. 1, with a film thickness h, which is an item of cross-sectional shape information about the test pattern that is obtained by the scatterometry process, a tilt angle θn at the measurement position n is determined when the cross-section is considered as a trapezoid.

Actually, as shown in FIG. 4(a), the cross-section of the sample is not a trapezoid, but has, for example, a bottom roundness and a rounded top edge. In such a case, a first-order differentiation waveform, as shown in FIG. 4(c), is obtained from an electron beam image signal (shown in FIG. 4(b)) of a device pattern, which signal is detected by the SEM, to quantify the average slope angle $\tan^{-1}(H/E)$, where H is the height when the cross section is considered as a trapezoid and E is the width between the top and bottom of the slope when viewed from above the pattern). The ratio of the bottom roundness B/H, where, in the first-order differentiation waveform, B is the width between the rising point corresponding to the bottom and the maximum point, and a ratio of the top roundness T/H, where, in the first-order differentiation waveform, T is the distance between the minimum point and the starting point of the flat portion corresponding to the top, are also obtained. Then, the shape of the pattern may be judged.

FIG. 5(b) shows a signal waveform of an electron beam image of a sample having a cross-sectional shape as shown in FIG. 5(a). The signal strength $SE_i$ of each point i on the slope is proportional to $1/\cos θ_i$ (relationship of an equation 5.1 of FIG. 5)($θ_i$ is a tilt angle of a sample). Therefore, the cross-sectional shape may be determined as follows.

The equation 5.1 of FIG. 5(c) has two unknowns a and b. The cross sectional shape may be determined through the following procedure. The unknowns a and b are determined using, e.g., a least-squares method, so that a result of integrating $d \tan θ_i$ (i=0 to N) produces the film thickness H (relationship of equation 5.2 of FIG. 5(c), where d is 1/N times the width between the top and bottom of a slope surface corresponding to E of FIG. 4(b)), and substituted for the equation 5.1 of FIG. 5(c).

Second Embodiment

Figure 6:
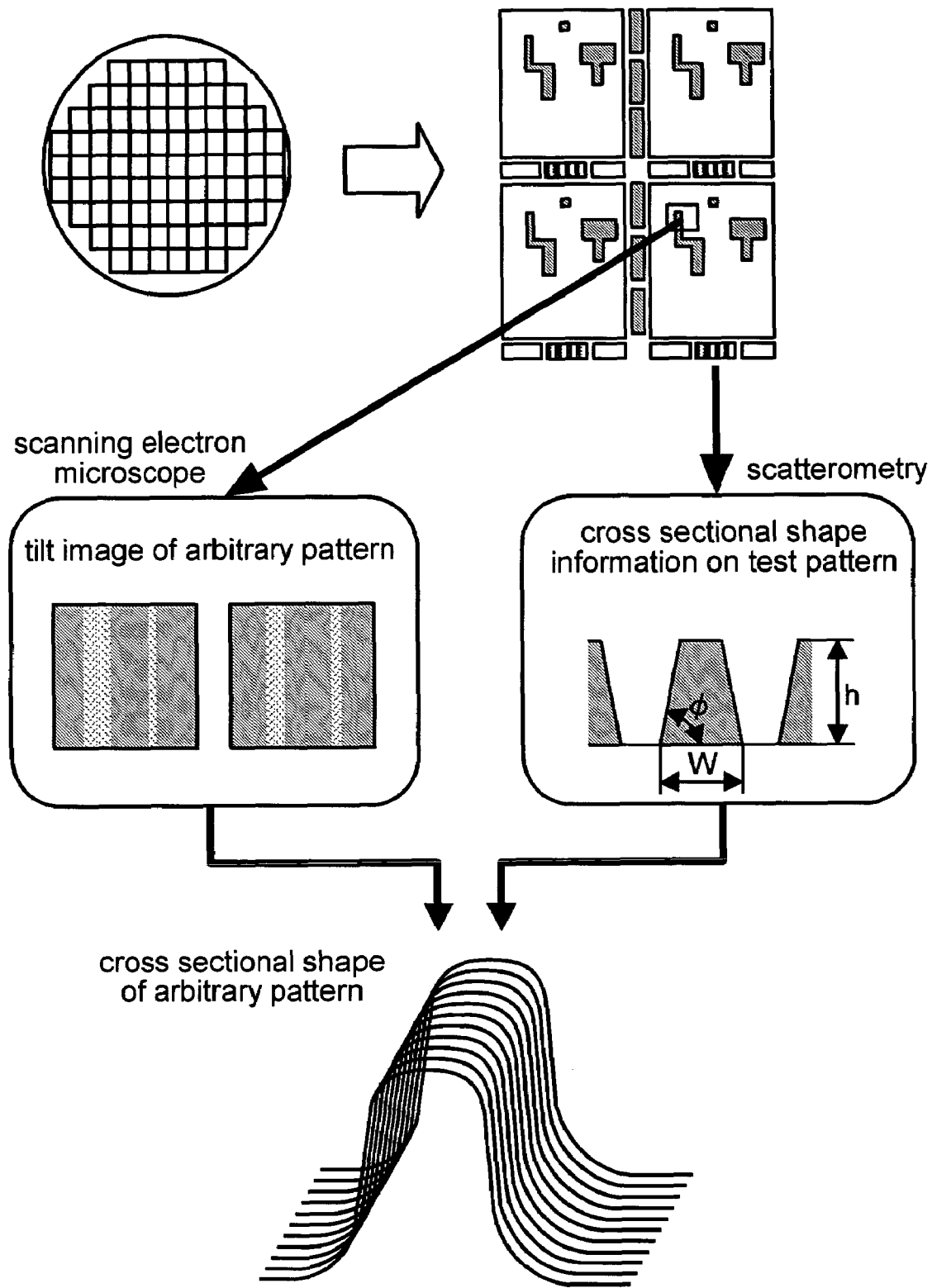
FIG. 6 is a diagram which shows a procedure for measurement in accordance with a second embodiment of the present invention.

FIG. 6 shows the principles employed in a second embodiment of the present invention.

In the present embodiment, on the principle of stereoscopic processing, a three dimensional shape of a sample is obtained from a plurality of images of the sample whose tilt angle changes using an electron microscope having a beam tilt or stage tilt system. FIG. 7(a) shows the electron beam image when the tilt angle of the sample is α1, and 7(b) shows the electron beam image when the tilt angle of the sample is α2. As shown in FIGS. 7(c) and 7(d), because the width of the side surface, when viewed from vertically above the sample, changes depending on the tilt angle, the widths of the bright bands of FIGS. 7(a) and 7(b) are different.

The bright band widths E1 and E2 of the images are measured to determine a tilt angle θ of the side surface. The tilt angle θ is inserted in an equation 7.2 to determine the height H0. The widths E1 and E2 change depending on the measurement points of an actual sample. Thus, it is necessary to determine which point on FIG. 7(b) corresponds to the measurement point of the bright band width of FIG. 7(a). However, for example, when the surface of the sample is smooth, it is difficult to correctly determine the corresponding point. In this case, information about a film thickness h obtained by the scatterometry method can be used. Instead of determining the corresponding point, a plurality of candidate points can be previously determined, and the heights of the candidate points are determined by the equation 7.2 to exclude those candidate points having heights different from the film thickness h.

In FIGS. 7(a) to 7(d), only a starting point and ending point of the side surface are used as the corresponding points. When there are distinguishing points also along the surface due to, e.g., irregularities of the surface of the sample, these distinguishing points also may be added as corresponding points. The three dimensional shape obtained by the above-described method is useful also for grasping the condition of three dimensional side surface roughness.

Third Embodiment

Figure 8:
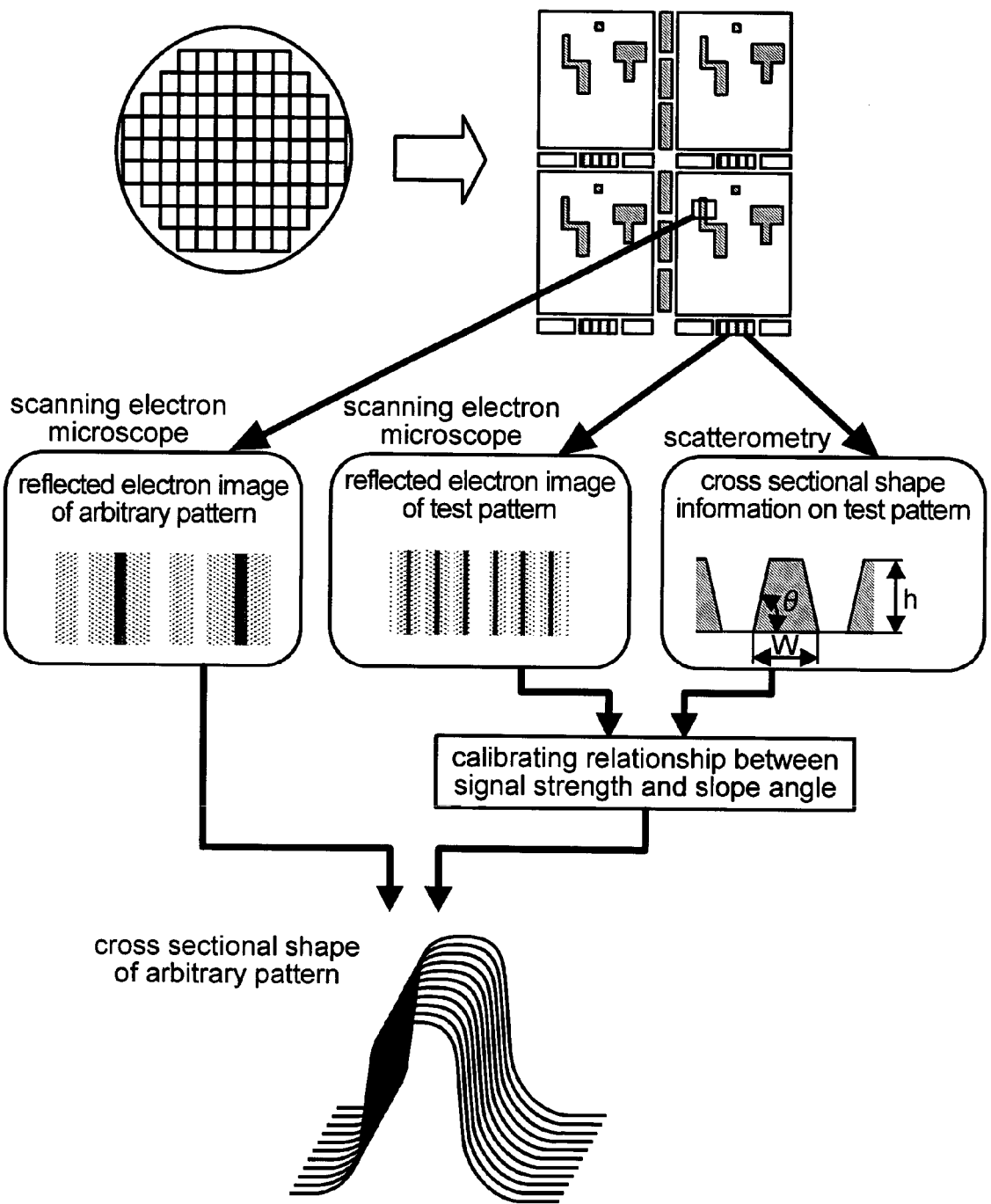
FIG. 8 is a diagram shows a procedure to be used for measurement in accordance with in a third embodiment of the present invention.

FIG. 8 shows the principles employed in a third embodiment of the present invention.

In this embodiment, on the principle of photometric stereo processing, as shown in FIGS. 9(a) to 9(e), a three dimensional shape of a sample is obtained from left and right reflected electron beam images (left and right reflected electron beam images are simultaneously obtained by right and left reflected electron beam detectors). FIGS. 9(a) and 9(b) show images and waveforms obtained by the left and right reflected electron beam detectors. In FIG. 9(a), the left side portion is brighter, and the shadowed right side portion is darker. In FIG. 9(b), the left side is darker, and the shadowed right side is brighter.

In an equation 9.1, K needs to be experimentally determined by measuring signal strengths A and B of a sample having a known slope angle θ. In this embodiment, a test pattern is measured by both scatterometry and a SEM, θ is determined from a result of measurement by scatterometry, and the signal strengths A and B are inserted in the equation 9.1 to determine K. Once K is determined, the cross-sectional shape can be determined from the signal strengths of reflected electron beam images of an arbitrary pattern. In the second embodiment, it was necessary to search for the corresponding points. In this embodiment, reflected electrons are simultaneously obtained by the two, right and left, reflected electron beam detectors, so that two images of the same point are obtained. As a result, it is not necessary to search the corresponding points.

The actual cross-sectional shape of the sample is not a trapezoid as shown in FIG. 9(c), but it has a constantly-changing slope angle, as shown in FIG. 9(e). Also, in this case, K is previously determined by measuring a test pattern by means of scatterometry and a SEM, and the slope angle θi of each point may be determined by an equation 9.3. The height H0 is determined by integrating tan θi. As a result, an arbitrary three dimensional shape can be determined from the right and left reflected electron beam images.

[Usage in Semiconductor Processing]

Figure 10:
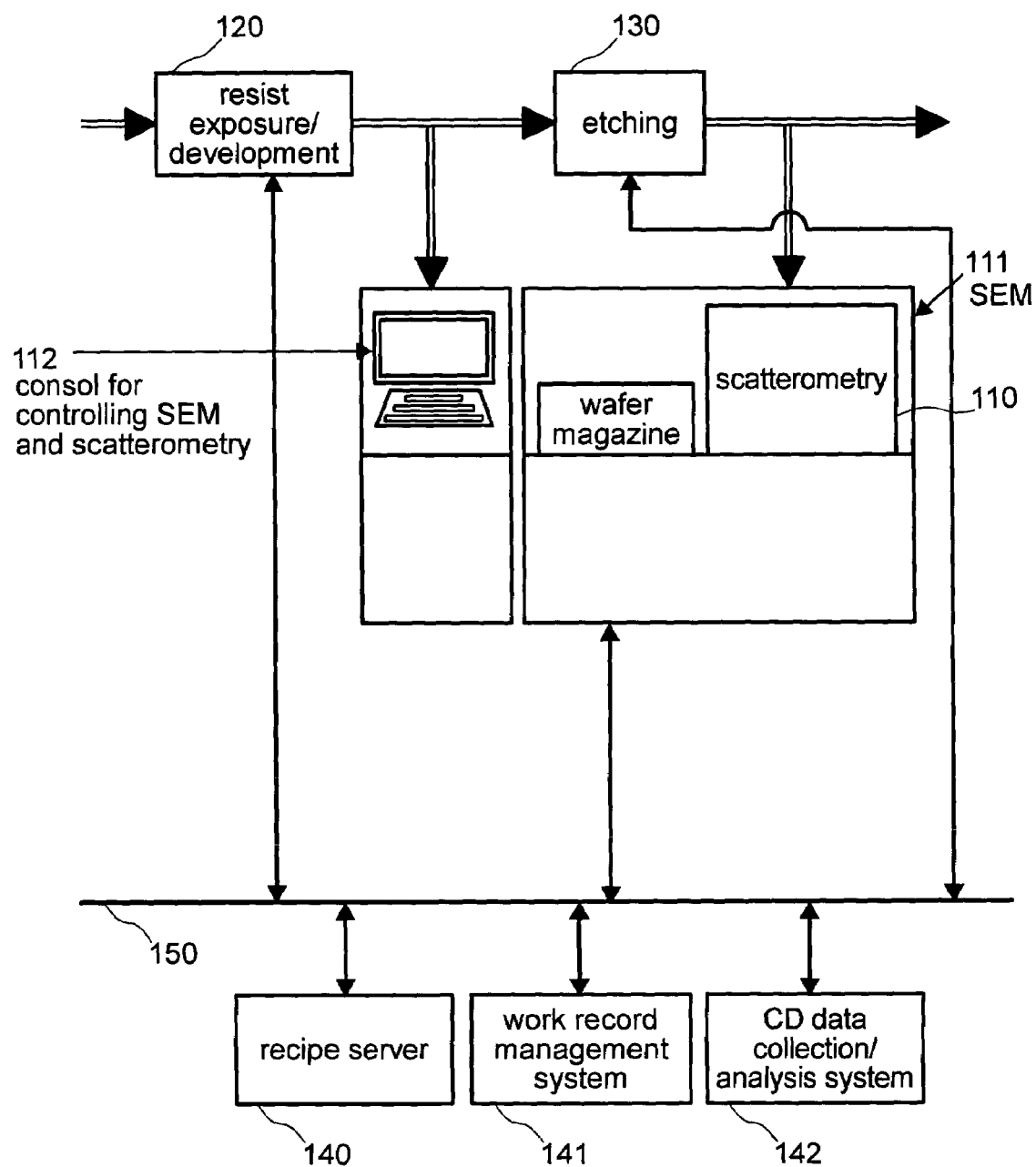
FIG. 10 is a block diagram showing how a method for measuring a three dimensional shape according to the present invention is used in a semiconductor processing line.

FIG. 10 shows how a method of measuring a three dimensional shape according to the present invention is used in semiconductor processing. A scatterometry device 110 and a SEM 111 are positioned close to each other, and they perform measurement before and after resist exposure/development processing 120 and etching processing 130 under control of a consol 112. The scatterometry device 110 and the SEM 111 are connected, e.g., to a recipe server 140, a work record management system 141, and a QC data collection/analysis system 142 via a communication line 150.

With such a system, the scatterometry device 110 and the SEM 111 measure three dimensional shapes of resist patterns formed on a wafer through the resist exposure/development processing 120 so as to monitor the resist exposure/development processing 120.

The scatterometry device 110 and the SEM 111 measure three dimensional shapes of semiconductor devices and circuit patterns that are formed on a wafer through the etching processing 130 in order to monitor the etching processing 130.

The three dimensional shape measurement data of the resist patterns and that of the element and circuit patterns are transmitted via the communication line 150 to the QC data collection/analysis system 142, where the relationship between both data is analyzed. In accordance with the analysis result and work record data stored in the work record management system 141, resist exposure/development processing and etching processing recipes stored in the recipe server 140 can be controlled.

[Method for Displaying Results]

Figure 12:
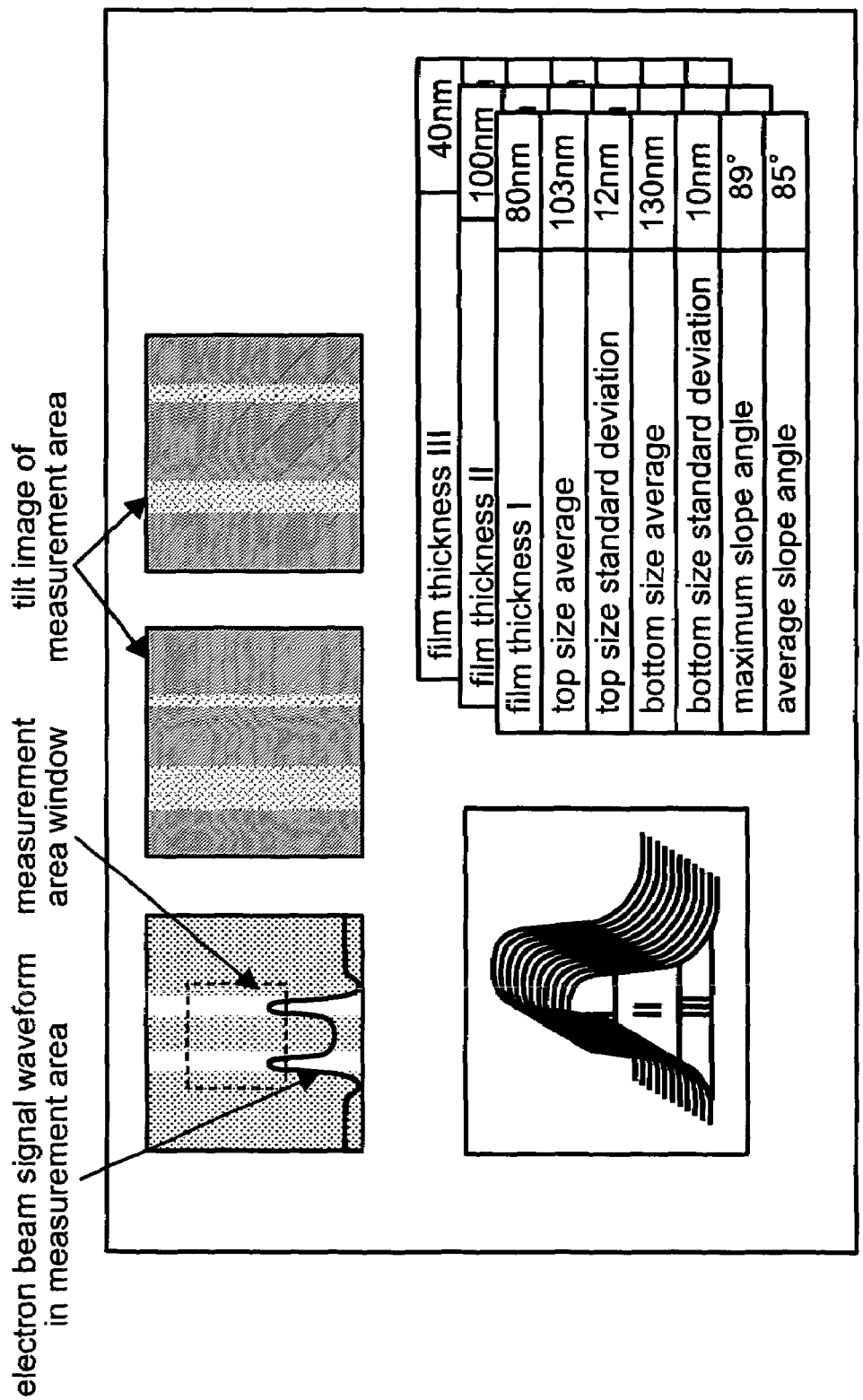
FIG. 12 is diagram of a display screen displaying a result of measurement in accordance with the second embodiment of the present invention.
Figure 13:
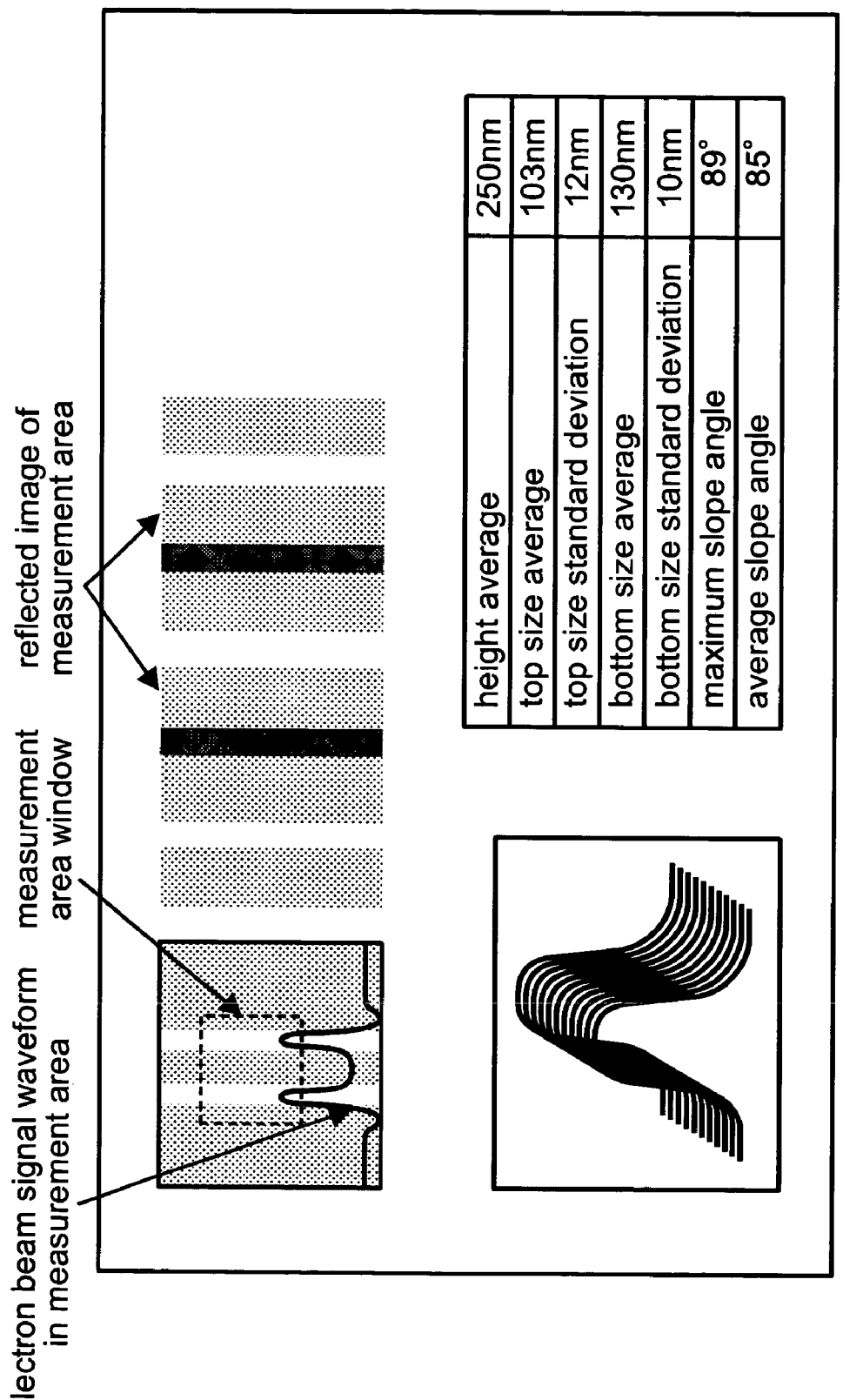
FIG. 13 is a diagram of a display screen displaying a result of measurement in accordance with the third embodiment of the present invention.

FIGS. 12 and 13 show examples of screens which display results of three-dimensional measuring patterns obtained by means of the scatterometry device 110 and the SEM 111.

FIG. 12 shows an example of a display screen of the second embodiment. A SEM image, two types of tilt images, and a result of three dimensional measurement are displayed within one screen. The SEM image shows the area where the two types of tilt images are observed. An electron beam signal waveform within the area is superimposed on the SEM image and displayed. This electron beam signal waveform may be a signal waveform for one typical scanning line, for a summation of a plurality of scanning lines, or for the combination of all of the signals detected in the area where the two types of tilt images are observed (many scanning lines are combined to obtain a waveform having an excellent S/N ratio).

A diagram showing the cross-sectional shape of the pattern and shape data of each portion of the cross-section are displayed as a result of the three dimensional measurement. When the pattern is formed of a plurality of layers, cross-sectional shape data of each layer may be displayed.

FIG. 13 shows an example of a display screen of the third embodiment. A SEM image, two types of tilt images, and a result of three dimensional measurement are displayed within one screen. The SEM image shows the area where the two types of tilt images are observed. An electron beam signal waveform within the area is superimposed on the SEM image and displayed.

Like the display in FIG. 12, this electron beam signal waveform may be a signal waveform for one typical scanning line, for a summation of a plurality of scanning lines, or for the combination of all of the signals detected in the area where the two types of reflected electron beam images are observed (many scanning lines are combined to obtain a waveform having an excellent a S/N ratio).

A diagram showing the cross-sectional shape of the pattern and shape data of each portion of the cross-section are displayed as a result of the three dimensional measurement. Cross-sectional shape data of each layer also may be displayed. This is because, when the pattern is formed of a plurality of layers, the detection signal changes depending on the secondary electron emission efficiency of each layer, so that each layer can be recognized to determine the cross-sectional shape data of each layer.

As described above, according to the present invention, the three dimensional shape of a fine pattern formed on a semiconductor device, such as a semiconductor memory and an integrated circuit, can be measured more precisely without deconstructing the semiconductor device.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description and all changes which come within the meaning and range of equivalency of the claims are therefore intended to be embraced therein.

What is claimed is:

1. A method of measuring a three dimensional shape of a fine pattern formed on a substrate, comprising the steps of:
   obtaining height information about the fine pattern by measuring the substrate;
   obtaining electron beam image information about the fine pattern by imaging the substrate by means of an electron microscope; and
   measuring the three dimensional shape of the fine pattern by use of the height information and the electron beam image information;
   wherein the electron beam image information includes information of average slope angle of a side wall of the fine pattern, information of a ratio of bottom roundness of the fine pattern and information of a ratio of top roundness of the fine pattern;
   wherein the information of average slope angle of a sidewall of the fine pattern is quantified by using information of a first-order differential waveform of a signal detected by the electron microscope of an average slope angle $\tan^{-1}(H/E)$, where H is a height when a cross section is considered as a trapezoid and E is a width between a top and bottom of the slope when viewed from above the fine pattern, the information of the ratio of bottom roundness of the fine pattern is quantified by using information of a first-order differential waveform of the ratio of the bottom roundness B/H, where B is the width between a rising point corresponding to a bottom and a maximum point, and the information of the ratio of top roundness of the fine pattern is quantified by using information of a first-order differential waveform of the ratio of the top roundness T/H, where T is a distance between a minimum point and a starting point of a flat portion corresponding to the top of the electron beam image signal.

2. The method of claim 1, wherein a test pattern is formed on the substrate, and the height information about the fine pattern is obtained from height information about the test pattern determined by measuring the test pattern.

3. The method of claim 1, wherein the height information about the fine pattern is obtained from information obtained from scatterometry.

4. The method of claim 1, wherein the electron beam image information about the fine pattern includes plane information about the fine pattern and side slope change information about the fine pattern, and a three dimensional shape of the fine pattern is measured by combining the plane information and side slope change information with the height information about the fine pattern.

5. The method of claim 1, wherein the electron microscope comprises a plurality of reflected electron detectors, the electron beam image information about the fine pattern is information obtained from a plurality of electron beam images detected by the plurality of reflected electron detectors.

6. The method of claim 5, wherein a three dimensional shape of the fine pattern is measured on the principle of photometric stereo processing by use of a plurality of the electron beam images detected by the plurality of reflected electron detectors.

7. A method of measuring a three dimensional shape of a fine pattern formed on a substrate, the pattern being in a form of a thin film, comprising the steps of:
   obtaining height information about a first pattern by measuring the first pattern;
   obtaining electron beam image information about a second pattern by imaging, using an electron microscope, the second pattern being formed on the substrate; and
   measuring a three dimensional shape of the second pattern by use of the height information about the first pattern and the electron beam image information about the second pattern;
   wherein the electron beam image information includes information of average slope angle of a side wall of the second pattern, information of a ratio of bottom roundness of the second pattern and information of a ratio of top roundness of the second pattern;
   wherein the information of average slope angle of a sidewall of the fine pattern is quantified by using information of a first-order differential waveform of a signal detected by the electron microscope of an average slope angle $\tan^{-1}(H/E)$, where H is a height when a cross section is considered as a trapezoid and E is a width between a top and bottom of the slope when viewed from above the pattern, the information of the ratio of bottom roundness of the fine pattern is quantified by using information of a first-order differential waveform of the ratio of the bottom roundness B/H, where B is the width between a rising point corresponding to a bottom and a maximum point, and the information of the ratio of top roundness of the fine pattern is quantified by using information of a first-order differential waveform of the ratio of the top roundness T/H, where T is a distance between a minimum point and a starting point of a flat portion corresponding to the top of the electron beam image signal.

8. The method of claim 7, wherein a height of the second pattern is estimated from the height information about the first pattern, and the estimated height information about the second pattern and the electron beam image information about the second pattern are used to measure a three dimensional shape of the second pattern.

9. A method of measuring a three dimensional shape of a fine pattern formed on a substrate, comprising the steps of:

obtaining height information about a fine pattern formed on the substrate by measuring the substrate;

obtaining a plurality of electron beam image information about the fine pattern formed on the substrate by imaging the substrate by means of an electron microscope;

measuring a three dimensional shape of the fine pattern by use of the obtained height information about the fine pattern and the obtained plurality of electron beam image information; and displaying, on a screen, information about the measured three dimensional shape of the fine pattern and a plurality of electron beam images of the fine pattern;

wherein in the step of measuring, the electron beam image information includes information of average slope angle of a side wall of the fine pattern, information of a ratio of bottom roundness of the fine pattern and information of a ratio of top roundness of the fine pattern;

wherein the information of average slope angle of a sidewall of the fine pattern is quantified by using information of a first-order differential waveform of a signal detected by the electron microscope of an average slope angle $\tan^{-1}$ (H/E), where H is a height when a cross section is considered as a trapezoid and E is a width between a top and bottom of the slope when viewed from above the fine pattern, the information of the ratio of bottom roundness of the fine pattern is quantified by using information of a first-order differential waveform of a ratio of the bottom roundness B/H, where B is the width between a rising point corresponding to a bottom and a maximum point, and the information of the ratio of top roundness of the fine pattern is quantified by using information of a first-order differential waveform of the ratio of the top roundness T/H, where T is a distance between a minimum point and a starting point of a flat portion corresponding to the top of the electron beam image signal.

10. The method of claim 9, wherein a waveform of a combination of a plurality of scanning line signals of one of the plurality of electron beam images of the fine pattern is displayed on the screen.

11. The method of claim 9, wherein the information obtained by measuring the substrate is information obtained by measuring a test pattern, formed on the substrate, by means of scatterometry.

12. The method of claim 9, wherein the electron beam image information obtained by imaging the substrate by means of the electron microscope is information obtained from a plurality of electron beam images detected by a plurality of reflected electron detectors equipped in the electron microscope.

13. An apparatus for measuring a three dimensional shape of a fine pattern formed on a substrate, comprising:

input means which input data obtained by measuring a first pattern repeatedly formed on a substrate and an electron beam image data of a second pattern finely formed on the substrate obtained by an electron microscope;

processing means which processes the data obtained by measuring the first pattern and the electron beam image data obtained by the electron microscope input by the input means to obtain a three dimensional shape of the second pattern; and output means which output data processed by the processing means through a communication line;

wherein the processing means processes the data obtained from the electron microscope by extracting information from the electron beam image data including information of average slope angle of a side wall of the second pattern, information of a ratio of bottom roundness of the second pattern and information of a ratio of top roundness of the second pattern;

wherein the output means outputs said data to a recipe server through the communication line, and wherein the processing means extracts the information including the information of average slope angle of a side wall of the fine pattern which is quantified by using information of a first-order differential waveform of a signal detected by the electron microscope of an average slope angle $\tan^{-1}$ (H/E), where H is a height when a cross section is considered as a trapezoid and E is a width between a top and bottom of the slope when viewed from above the fine pattern, the information of the ratio of bottom roundness of the fine pattern which is quantified by using information of a first-order differential waveform of the ratio of the bottom roundness B/H, where B is the width between a rising point corresponding to a bottom and a maximum point, and the information of the ratio of top roundness of the fine pattern which is quantified by using information of a first-order differential waveform of the ratio of the top roundness T/H, where T is a distance between a minimum point and a starting point of a flat portion corresponding to the top of the electron beam image signal.

14. An apparatus according to claim 13, further comprising a display means which displays an electron beam image input through the input means together with an image of the three dimensional shape of the second pattern obtained by the processing means and a list of information of the three dimensional shape of the second pattern.

* * * * *